United States Patent
Dingmann et al.

(10) Patent No.: US 9,662,210 B2
(45) Date of Patent: May 30, 2017

(54) SYSTEM FOR TESTING VALVES

(71) Applicant: TA INSTRUMENTS-WATERS L.L.C., Milford, MA (US)

(72) Inventors: David L. Dingmann, Saint Paul, MN (US); Troy D. Nickel, Minneapolis, MN (US); Andrew D. White, Minneapolis, MN (US); Kyle P. Duffin, Shakopee, MN (US); Ryan Siskey, Philadelphia, PA (US); Michael Liebschner, Pearland, TX (US); Andrew Rau, Philadelphia, PA (US); Sunoj Narayanan, Eden Prairie, MN (US); Lito Cruz Mejia, Savage, MN (US)

(73) Assignee: TA Instruments-Waters L.L.C., Milford, MA (US)

( * ) Notice: Subject to any disclaimer, the term of this patent is extended or adjusted under 35 U.S.C. 154(b) by 282 days.

(21) Appl. No.: 14/306,508

(22) Filed: Jun. 17, 2014

(65) Prior Publication Data

US 2015/0359633 A1     Dec. 17, 2015

(51) Int. Cl.
    *G01N 17/00*     (2006.01)
    *A61F 2/24*     (2006.01)

(52) U.S. Cl.
    CPC ............................. *A61F 2/2472* (2013.01)

(58) Field of Classification Search
    USPC .......................................................... 73/865.6
    See application file for complete search history.

(56) References Cited

U.S. PATENT DOCUMENTS

| | | | |
|---|---|---|---|
| 3,376,660 A | 4/1968 | McGinnis | .................... 434/268 |
| 4,546,642 A * | 10/1985 | Swanson | ............... A61F 2/2472 73/168 |
| 4,682,491 A * | 7/1987 | Pickard | ................. A61F 2/2472 73/168 |
| 5,052,934 A | 10/1991 | Carey et al. | |
| 5,176,153 A * | 1/1993 | Eberhardt | ............. A61F 2/2472 128/897 |
| 5,670,708 A | 9/1997 | Vilendrer | |
| 6,863,123 B2 * | 3/2005 | Wang | ........................ F25D 3/10 165/263 |
| 6,881,224 B2 | 4/2005 | Kruse et al. | ................. 623/2.11 |
| 8,444,935 B2 * | 5/2013 | Nickel | ..................... G01N 3/12 422/505 |
| 8,490,504 B2 | 7/2013 | Weinberg et al. | ........... 73/865.6 |
| 8,584,538 B2 | 11/2013 | McCloskey et al. | ........ 73/865.6 |

(Continued)

FOREIGN PATENT DOCUMENTS

| | | |
|---|---|---|
| WO | 2014/000105 | 1/2014 |
| WO | WO-2014/000105 A1 | 1/2014 |

OTHER PUBLICATIONS

International Search Report for international application No. PCT/US2015/036293, filing date Jun. 17, 2015.

(Continued)

*Primary Examiner* — Clayton E LaBalle
*Assistant Examiner* — Warren K Fenwick
(74) *Attorney, Agent, or Firm* — McCarter & English, LLP; Deborah M. Vernon; Vadim Cherkasov

(57) ABSTRACT

This document provides systems and methods for testing of various kinds of valves. For example, this document provides systems and methods for accelerated life testing of prosthetic heart valves.

20 Claims, 11 Drawing Sheets

(56) References Cited

U.S. PATENT DOCUMENTS

| | | | |
|---|---|---|---|
| 8,627,708 B2 | 1/2014 | McCloskey et al. ............. 73/37 |
| 2010/0225478 A1 | 9/2010 | McCloskey et al. |
| 2010/0313683 A1* | 12/2010 | Nickel .................... G01N 3/12 |
| | | | 73/863 |
| 2011/0303026 A1* | 12/2011 | Lee ....................... A61F 2/2472 |
| | | | 73/866.4 |
| 2013/0233397 A1 | 9/2013 | McCloskey et al. ........... 137/12 |
| 2014/0076029 A1* | 3/2014 | Lee ....................... A61F 2/2472 |
| | | | 73/37 |
| 2014/0109651 A1 | 4/2014 | McCloskey et al. ............. 73/37 |
| 2015/0359634 A1* | 12/2015 | Dingmann ............... G01N 3/00 |
| | | | 73/865.6 |
| 2016/0230619 A1* | 8/2016 | McCarthy, Jr. ..... F01L 13/0005 |

OTHER PUBLICATIONS

Reul et al., "Durability/Wear Testing of Heart Valve Substitutes," J. Heart Valve Dis. 7(2): 151-157 (1998).

\* cited by examiner

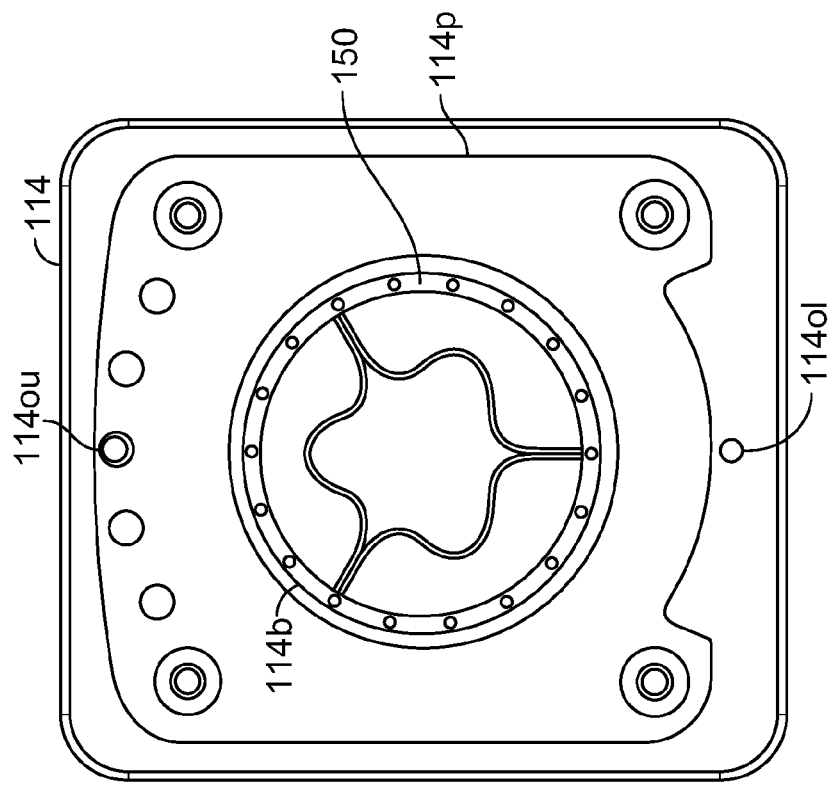
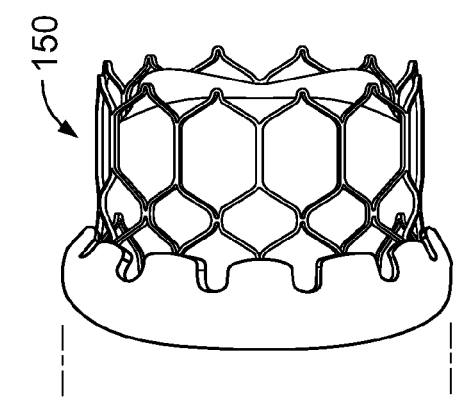
FIG. 6A
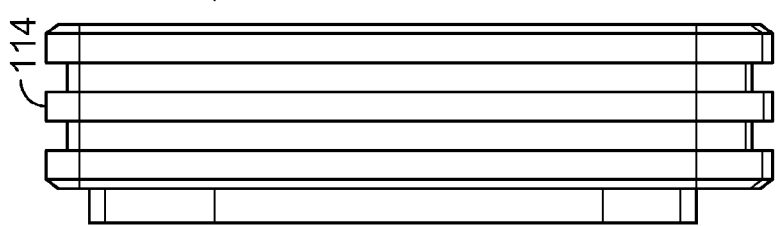
FIG. 6B

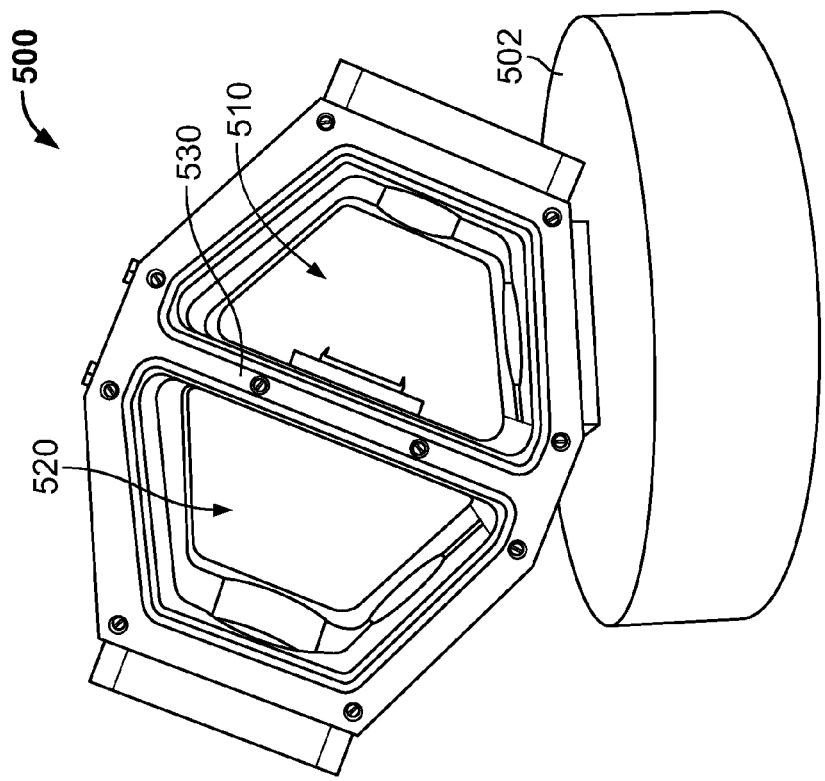
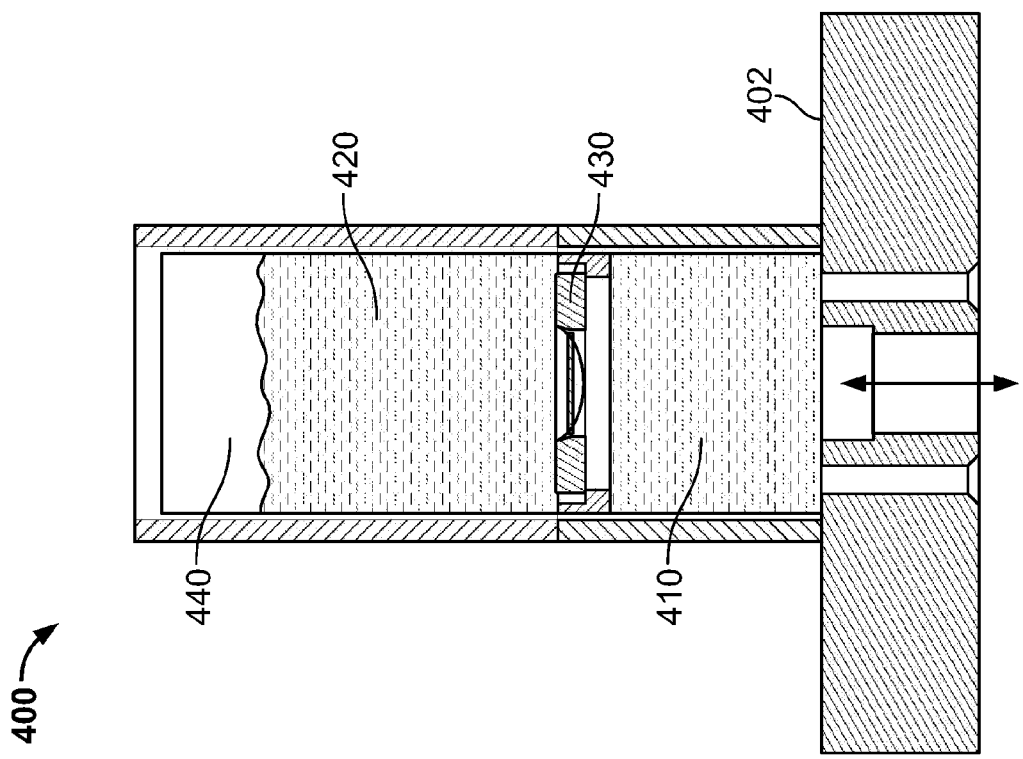

SYSTEM FOR TESTING VALVES

BACKGROUND

1. Technical Field

This document relates to systems and methods for testing valves. For example, this document relates to systems and methods for accelerated life testing of prosthetic heart valves.

2. Background Information

Accelerated life testing (also known as accelerated wear testing or durability testing) is the process of testing an item by subjecting it to conditions (e.g., cycle time, stress, strain, temperatures, voltage, vibration, pressure, etc.) in excess of its normal service parameters in an effort to uncover faults and potential modes of failure in a reduced amount of time. Accelerated life testing can be been used to study materials, design concepts, design modifications, and durability variations caused by changes in manufacturing techniques.

The ISO 5840-3:2013 standard outlines an approach for qualifying the design and manufacture of heart valve prostheses. ISO 5840-3:2013 requires that mechanical heart valves be tested for at least 600 million cycles (equivalent to 15 years in vivo), and that biological heart valve prostheses be tested for at least 200 million cycles (equivalent to 5 years in vivo) in pulsatile flow simulators using a range of pressures seen in physiologic conditions. The cyclic test must also meet the following two requirements: 1) the test valve must open and close sufficiently each cycle, and 2) during at least 5% of each cycle, the differential pressure across the valve (transvalvular $\Delta P$) must be at least a specified pressure (e.g., 100 mmHg for aortic valves and 120 mmHg for mitral valves).

SUMMARY

This document provides systems and methods for testing various kinds of valves. For example, this document provides systems and methods for accelerated life testing of prosthetic heart valves. The systems and methods provided herein are well-suited for use with a wide variety of types of prosthetic and biological heart valves. For example, prosthetic heart valves that are intended for deployment at anatomical sites including, but not limited to, aortic valves, mitral valves, atrioventricular valves, pulmonary valves, and the like, can be tested using the systems and methods provided herein. Further, valve types such as, but not limited to, mechanical valves, tissue (biological) valves, tissue-engineered valves, surgically implantable valves, transcatheter implantable valves, and the like, can be subjected to accelerated life testing using the systems and methods provided herein. The systems and methods provided herein can also be used for accelerated life testing of non-medically related valves.

In one implementation, a chamber assembly for testing a valve includes a proximal chamber portion that defines a proximal interior space, a distal chamber portion that defines a distal interior space that is confluent with the proximal interior space, and a valve holder that is disposed between the proximal interior space and the distal interior space. The valve holder is configured to receive the valve in a bore of the valve holder. The valve holder includes one or more return flow orifices such that the proximal interior space is in fluid communication with the distal interior space via the one or more return flow orifices.

Such a chamber assembly may optionally include one or more of the following features. The chamber assembly may be configured such that when the chamber assembly is coupled to an accelerated life testing system, and when the valve is contained in the bore of the valve holder, a bottom of the valve and a top of the valve are both visible by an observer. The chamber assembly may define a longitudinal axis, and the chamber assembly may be configured such that when the chamber assembly is coupled to an accelerated life testing system the longitudinal axis is tilted at an angle in comparison to horizontal. The angle may be between about 20° and about 70° from horizontal. An open area of the one or more return flow orifices may be adjustable without removing the valve holder from the chamber assembly. The chamber assembly may further comprise a first pressure sensor configured to measure a liquid pressure within the proximal interior space and a second pressure sensor configured to measure a liquid pressure within the distal interior space. The chamber assembly may further comprise one or more lights coupled to the chamber assembly and configured for illuminating the valve. The distal chamber portion may be releasably attachable to the proximal chamber portion. The valve holder may be removably disposed between the proximal interior space and the distal interior space. The chamber assembly may be configured for accelerated life testing of the valve. The chamber assembly may be configured to contain a liquid. The one or more return flow orifices may be positioned on the valve holder such that at least a first return flow orifice of the one or more return flow orifices is located in an upper portion of the chamber and at least a second return flow orifice of the one or more return flow orifices is located in a lower portion of the chamber. The bore of the valve holder may be at least partially defined by a compliant sleeve that is configured to receive the valve, and the compliant sleeve may be configured to deflect in response to a pressure differential between the proximal interior space and the distal interior space. Three or more sides of the chamber assembly may be substantially transparent. An open area of the one or more return flow orifices may be selected based on a size of a valve to be tested.

In another implementation, system for testing a valve includes a chamber assembly, a fluid displacement member, and an actuator that is configured to actuate the fluid displacement member. The chamber assembly comprises a proximal chamber portion that defines a proximal interior space, a distal chamber portion that defines a distal interior space that is confluent with the proximal interior space, and a valve holder that is disposed between the proximal interior space and the distal interior space. The valve holder is configured to receive the valve in a bore of the valve holder. The valve holder includes one or more return flow orifices such that the proximal interior space is in fluid communication with the distal interior space via the one or more return flow orifices. The fluid displacement member defines a displacement member interior space that is confluent with the proximal interior space.

Such a system for testing a valve may optionally include one or more of the following features. When the valve is contained in the bore of the valve holder and the valve holder is disposed between the proximal chamber and the distal chamber, a bottom of the valve and a top of the valve may both be visible by an observer. The chamber assembly defines a longitudinal axis, and when the chamber assembly is coupled with the fluid displacement member, the longitudinal axis may be tilted at an angle in comparison to vertical. The system angle may be between about 20° and about 70° from vertical. The actuator may comprise a linear electromagnetic actuator. The system may further comprise a machine vision system that includes a camera configured to capture images of the valve as the valve is cycled between an open state and a closed state. The system may further comprise one or more lights coupled to the chamber assembly and configured for illuminating the valve. The system may further comprise a machine vision system that includes a camera configured to capture images of the valve, and a lighting controller configured to cause the one or more lights to be illuminated at a rate correlated to a rate of actuation of the fluid displacement member. The system may further comprise a first pressure sensor configured to measure a liquid pressure within the proximal interior space and a second pressure sensor configured to measure a liquid pressure within the distal interior space. The system may further comprise a flexible diaphragm disposed between the chamber assembly and the bellows, the flexible diaphragm separating the proximal interior space and the displacement member interior space. The actuator may comprise a rotary motor. The fluid displacement member may comprise a bellows. The fluid displacement member may comprise a rolling diaphragm. An open area of the one or more return flow orifices may be adjustable without removing the valve holder from the chamber assembly. The system may further comprise an orifice actuator that is configured to adjust the open area of the one or more return flow orifices at least in part in response to a signal from a control system. The distal chamber portion may be releasably attachable to the proximal chamber portion. The valve holder may be removably disposed between the proximal interior space and the distal interior space. The system may be configured for accelerated life testing of the valve. The system may further comprise a liquid disposed at least partially within the (i) displacement member interior space, (ii) proximal interior space, and (iii) distal interior space. The system may further comprise an airspace within the distal interior space.

In another implementation, a method for controlling an accelerated life testing system includes (i) receiving, by a computer controller of the system, an indication of an effective open area of a valve that is being cycled between an open state and a closed state by the accelerated life testing system, the effective open area corresponding to the open state, wherein the indication of the effective open area of the valve is received from a machine vision system that includes a camera that captures images of the valve as the valve is being cycled between the open state and the closed state; (ii) comparing, by the computer controller, the indication of the effective open area of the valve to a threshold value; and (iii) adjusting, by the computer controller and based on the comparing, an actuator of the accelerated life testing system, wherein the adjusting causes a change to the effective open area of the valve.

Such a method for controlling an accelerated life testing system may optionally include one or more of the following features. The adjusting may comprise increasing or decreasing an amplitude of an input waveform of the accelerated life testing system, wherein the input waveform is used to control the actuator. The method may further comprise adjusting, by the computer controller and based on a differential pressure across the valve, an orifice size, wherein the adjusting the orifice size causes a change to the differential pressure across the valve. The method may further comprise illuminating the valve, The illuminating the valve may be performed at a timing that is based on a rate at which the valve is being cycled between the open state and the closed state.

In another implementation, a system for testing a valve includes a chamber assembly, one or more lights coupled to the chamber assembly and configured for illuminating a valve, an oscillating fluid pump defining an interior pump space that is confluent with the proximal interior space, an actuator that is configured to actuate the oscillating fluid pump at a rate of actuation, thereby adjusting the interior pump space, and a control system that is configured to cause the one or more lights to illuminate at a rate correlated to the rate of actuation. The chamber assembly comprises a proximal chamber portion that defines a proximal interior space, a distal chamber portion that defines a distal interior space that is confluent with the proximal interior space, and a valve holder that is disposed between the proximal interior space and the distal interior space, the valve holder configured to receive the valve in a bore of the valve holder.

Such a system for testing a valve may optionally include one or more of the following features. The system may further comprise a camera configured to capture images of the valve as the valve is cycled between an open state and a closed state. The control system may comprise a machine vision system configured to determine an extent of openness of the valve when the valve is in the open state, and wherein an output from the camera is an input to the machine vision system. The control system may be configured to adjust the system in response to a determination that the extent of openness of the valve is below a threshold value. The valve holder may include one or more return flow orifices that define an open space such that the proximal interior space is in fluid communication with the distal interior space via the open space, and the control system may be configured to adjust a configuration of the open space in response to the determination that the extent of openness of the valve is below the threshold value. The chamber assembly may be a first chamber assembly and the system may further comprise one or more additional chamber assembly. The one or more additional chamber assembly each comprise: a proximal chamber portion that defines a proximal interior space; a distal chamber portion that defines a distal interior space that is confluent with the proximal interior space; and a valve holder that is disposed between the proximal interior space and the distal interior space, the valve holder configured to receive the valve in a bore of the valve holder. The first chamber assembly and the one or more additional chamber assembly may each be controlled by a computer system. The valve holder may be separable from the chamber assembly. The system may further comprise a diaphragm disposed between the chamber assembly and the oscillating fluid pump. The diaphragm may be configured to transmit a fluid pressure between the chamber assembly and the oscillating fluid pump. A first liquid may be contained in the chamber assembly and a second liquid that is different from the first liquid may be contained in the interior pump space. The valve holder may be configured to receive the valve in a first orientation and a second orientation that is rotated about 180 degrees from the first orientation.

Particular embodiments of the subject matter described in this document can be implemented to realize one or more of the following advantages. First, in some embodiments the accelerated life testing systems provided herein are capable of operating at a high rate of speed. For example, in some embodiments the systems can operate at about 30 Hz or above. As such, the duration of the accelerated life tests can be shortened in comparison to systems that operate at slower speeds. Second, in some embodiments the test requirement for the transvalvular ΔP to be at least a specified pressure during at least 5% of the cycle can be met with minimal ΔP overshoot. This feature can minimize valve overstress during the test process. Such overstress can cause overly harsh test conditions and may lead to unrepresentative test results.

Third, the pulsatile flow systems for accelerated life testing provided herein are configured for convenience of use. For example, in some embodiments portions of the test equipment can be removed from the pulsatile flow system and installed on other test equipment in a user-friendly manner. Fourth, the systems provided herein are configured to allow visual observation and analysis of the valves during the test process. Such visual analysis can be performed using normal eyesight, or using cameras such as, but not limited to, automated machine vision systems in some embodiments. Fifth, in some embodiments the systems provided herein are configured to substantially replicate physiological conditions and/or meet ISO test requirements while using a standard sine wave input waveform. However, in some embodiments non-sinusoidal waveforms may be used. Sixth, some aspects of the system (e.g., the test chamber) are designed to be adjustable to provide the fluid dynamic performance to meet the user's test requirements. That is, in some embodiments the fluid dynamic performance of the system can be tuned to achieve the performance desired by adjusting, for example, the return orifice size or air cavity size. What is more, in some embodiments closed loop controls for automatic system tuning during the test process are included.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 6A is an exploded side view of an example valve holder and prosthetic valve sub-assembly.

FIG. 6B is a front view of the valve holder and prosthetic valve sub-assembly of FIG. 6A.

FIG. 11 is a side view of another example embodiment of a test chamber for an accelerated life testing system in accordance with some embodiments.

FIG. 12 is a side view of another example embodiment of a test chamber for an accelerated life testing system in accordance with some embodiments.

Like reference numbers represent corresponding parts throughout.

DETAILED DESCRIPTION

This document provides systems and methods for testing various kinds of valves. For example, this document provides systems and methods for accelerated life testing of prosthetic heart valves.

Figure 1:
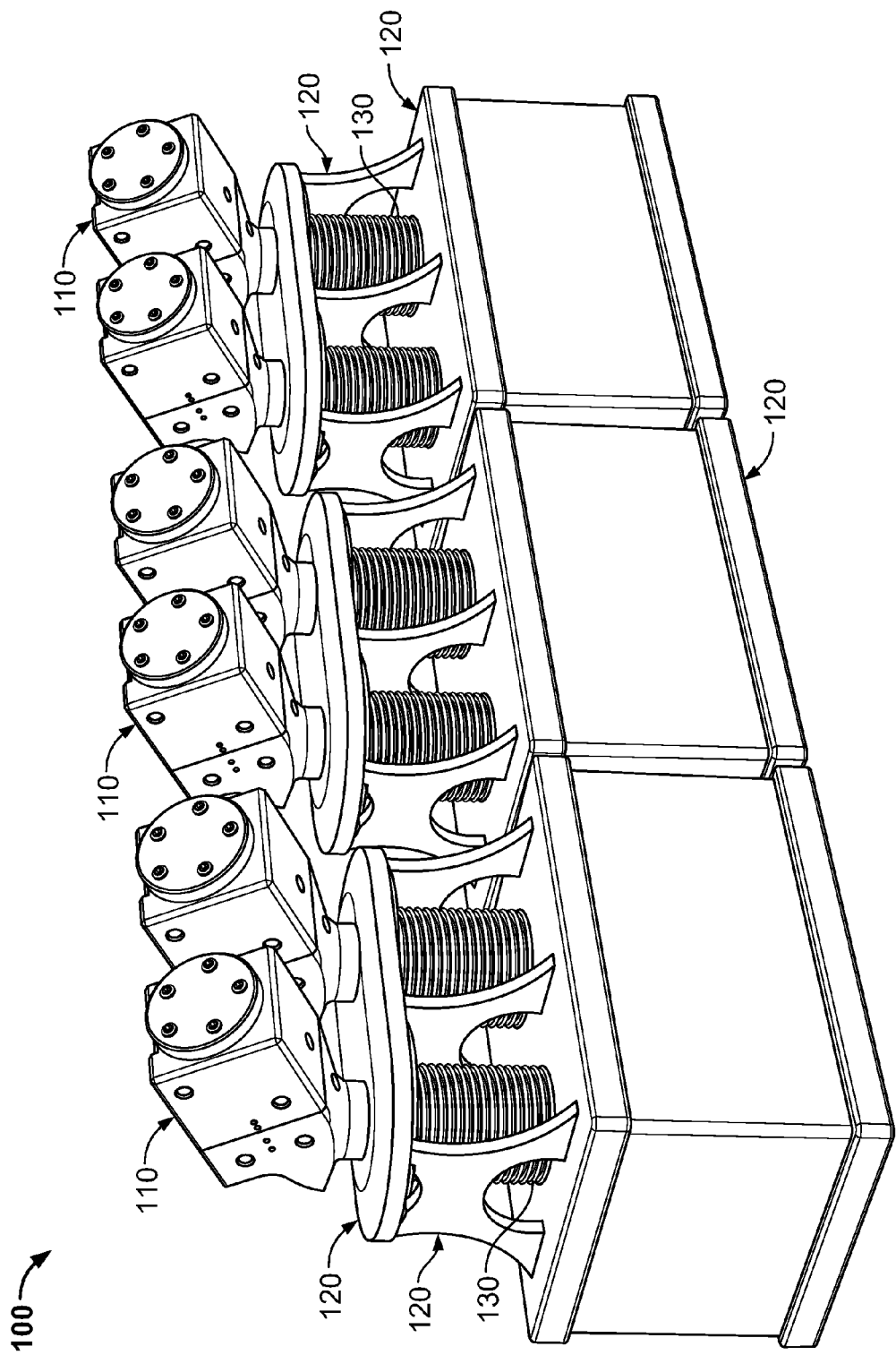
FIG. 1 is perspective view of an example accelerated life testing system in accordance with some embodiments.
Figure 2:
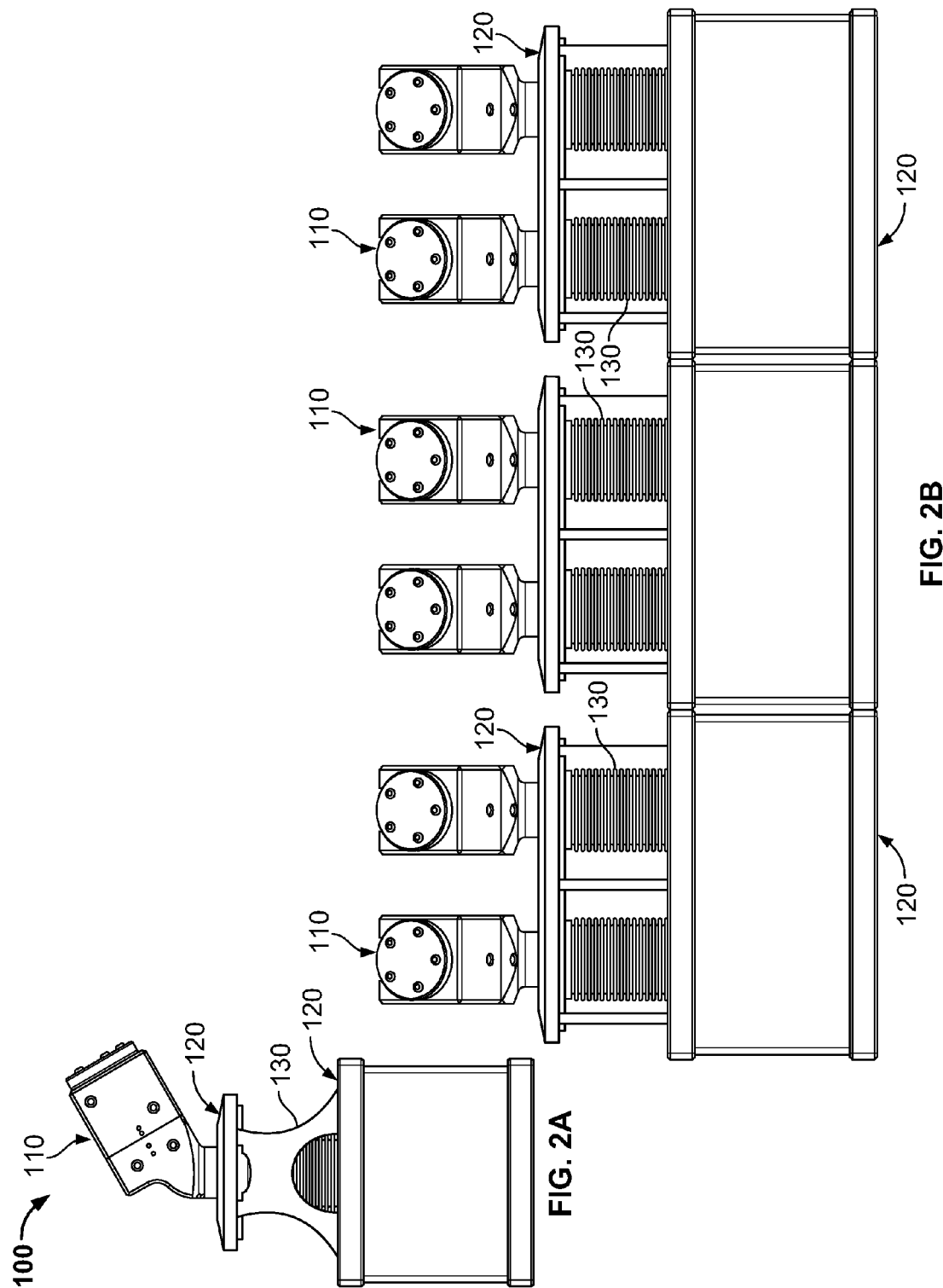
FIG. 2A is a side view of the accelerated life testing system of FIG. 1.
FIG. 2B is a front view of the accelerated life testing system of FIG. 1.

Referring to FIGS. 1, 2A, and 2B an example multi-station accelerated life testing (ALT) system 100 includes multiple chambers 110, a framework 120, and multiple bellows 130. The chambers 110 and the bellows 130 are mounted to and are supported by the framework 120. Each individual chamber 110 is in fluid communication with a corresponding individual bellows 130 located below the individual chamber 110, or a flexible membrane diaphragm 121 can be optionally used between the chamber 110 and bellows 130 in some embodiments. The bellows 130 can be axially extended or compressed, as will be described further below.

The internal spaces of the chamber 110 and the bellows 130 can receive a liquid (e.g., saline, water, and the like). Accordingly, an axial extension or compression of the bellows 130 will initiate a corresponding movement of the liquid within the bellows 130 and within the chamber 110. In regard to embodiments that include the optional flexible membrane diaphragm 121, such movements of the bellows 130 create pressure changes in the liquid contained in the bellows 130 that are communicated to the liquid in the chamber 110 via the flexible membrane diaphragm 121. As will be described further below, a valve (e.g., a prosthetic heart valve) can be mounted within the chamber 110. An axial actuation of the bellows 130 can therefore move a liquid through the valve such that the valve is cycled between an opened state and a closed state.

In the example ALT system 100, six stations that each include an individual chamber 110 and a corresponding individual bellows 130 are included. In other system embodiments, fewer or more than six stations can be included. For example, in one alternative embodiment an ALT system can include a single chamber 110 and a single corresponding bellows 130. In general, the ALT system 100 is scalable such that any practical number of test stations can be included.

Figure 3:
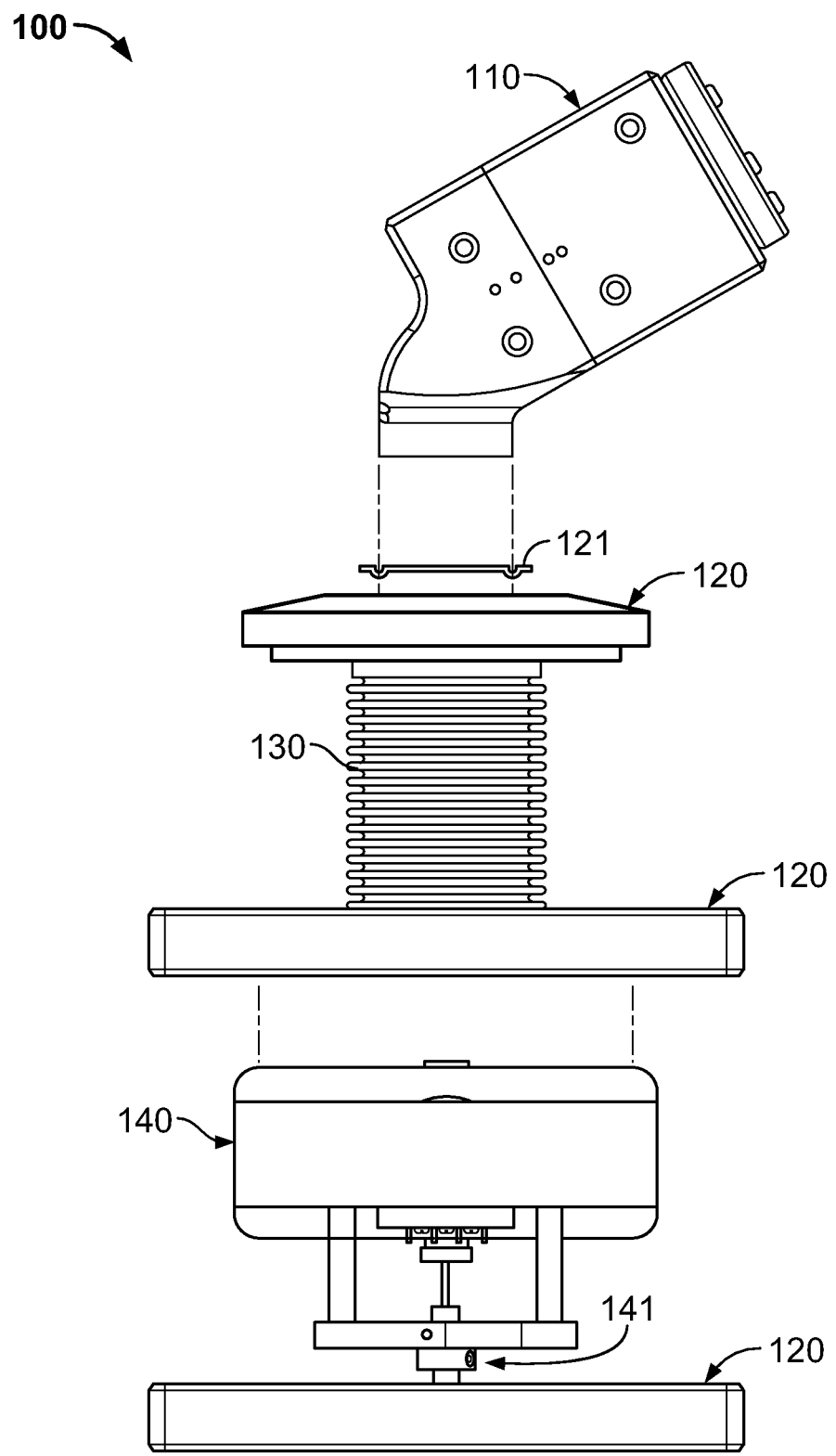
FIG. 3 is an exploded side view of the accelerated life testing system of FIG. 1.

Referring to FIG. 3, the ALT system 100 (shown in an exploded side view) can also include a linear actuator 140. The bottom end of the linear actuator 140 can be mounted to the framework 120, and the active end of the linear actuator 140 can be attached to the bellows 130. In some embodiments, an individual linear actuator 140 can be configured to drive two or more bellows 130.

In some embodiments, the linear actuator 140 is an electromagnetic actuator that includes one or more stator coils and flexural suspension elements that are connected to each end of an armature of the actuator 140. The flexural suspension elements allow frictionless movement of the armature in a vertical direction of travel while providing resistance to movement of the armature in other degrees of freedom (e.g., translation, rotation). During operation of the electromagnetic actuator 140, magnetic fields from a magnetic assembly that has one or more permanent magnets interact with the magnetic fields generated by the electrical current flowing in the stator wire coils. This interaction causes the armature to move linearly up and down relative to the housing framework 120. In some embodiments, a displacement sensor 141 (e.g., an LVDT, and the like) is optionally included to detect and acquire data regarding the linear movement of the actuator 140. The data output from the displacement sensor 141 can be used, for example, for closed-loop control of the actuator 140 in some embodiments. In some embodiments, the displacement sensor 141 can be used, for example, as an indicator for piston movement or to indicate fluid transfer per cycle with an established actuator to fluid volume relationship.

The linear movement of the actuator 140 induces, in turn, axial extension and compression of the bellows 130. A liquid inside of the bellows 130 will be withdrawn from or propelled into the chamber 110 to which the bellows 130 is attached. This movement of liquid can cause an opening and closing of a valve that is located within the chamber 110. In some embodiments, other types of fluid displacement members can be substituted for the bellows 130 (e.g., a sliding piston or a rolling diaphragm, and the like). In some embodiments, other types of actuator devices can be substituted for the linear electromagnetic actuator 140 (e.g., a rotary motor with a crank mechanism, and the like). Various combinations and sub-combinations of fluid displacement members and actuator devices are envisioned within the scope of this disclosure.

Figure 4B:
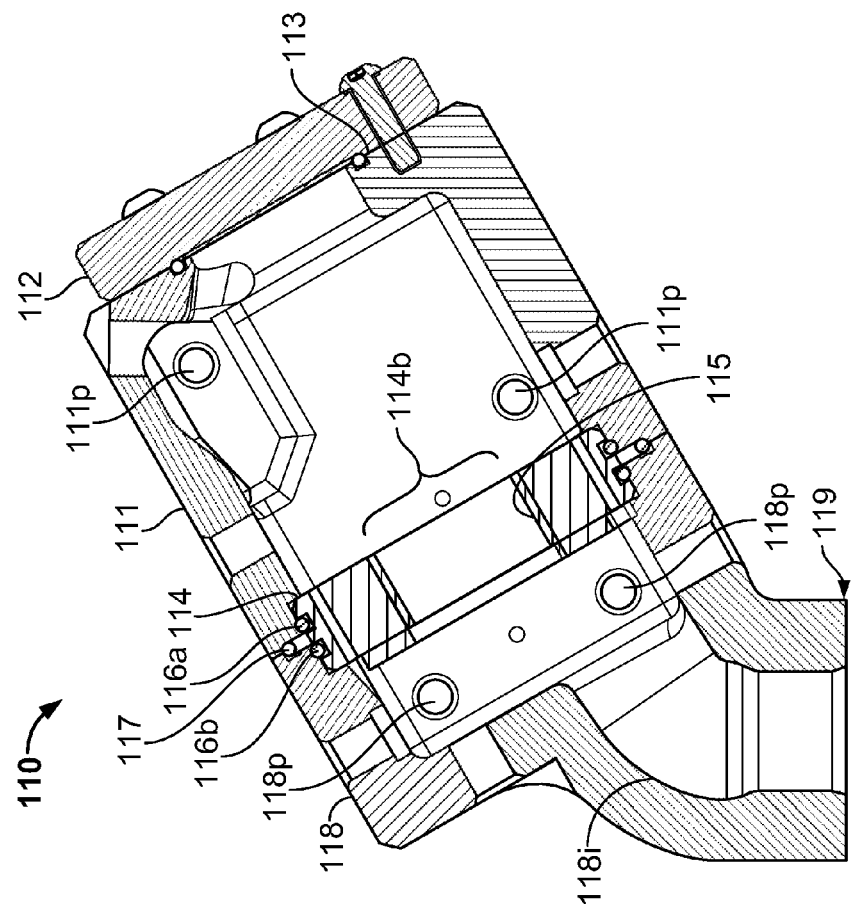
FIG. 4B is cross-sectional side view of the test chamber of FIG. 4A.
Figure 4A:
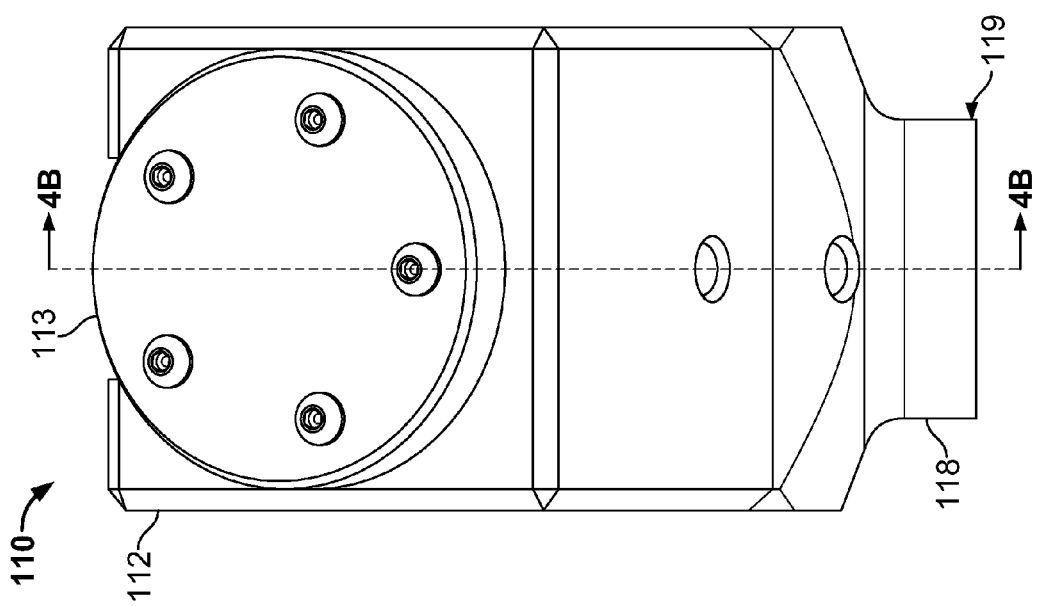
FIG. 4A is a front view of an example test chamber for an accelerated life testing system in accordance with some embodiments.
Figure 5:
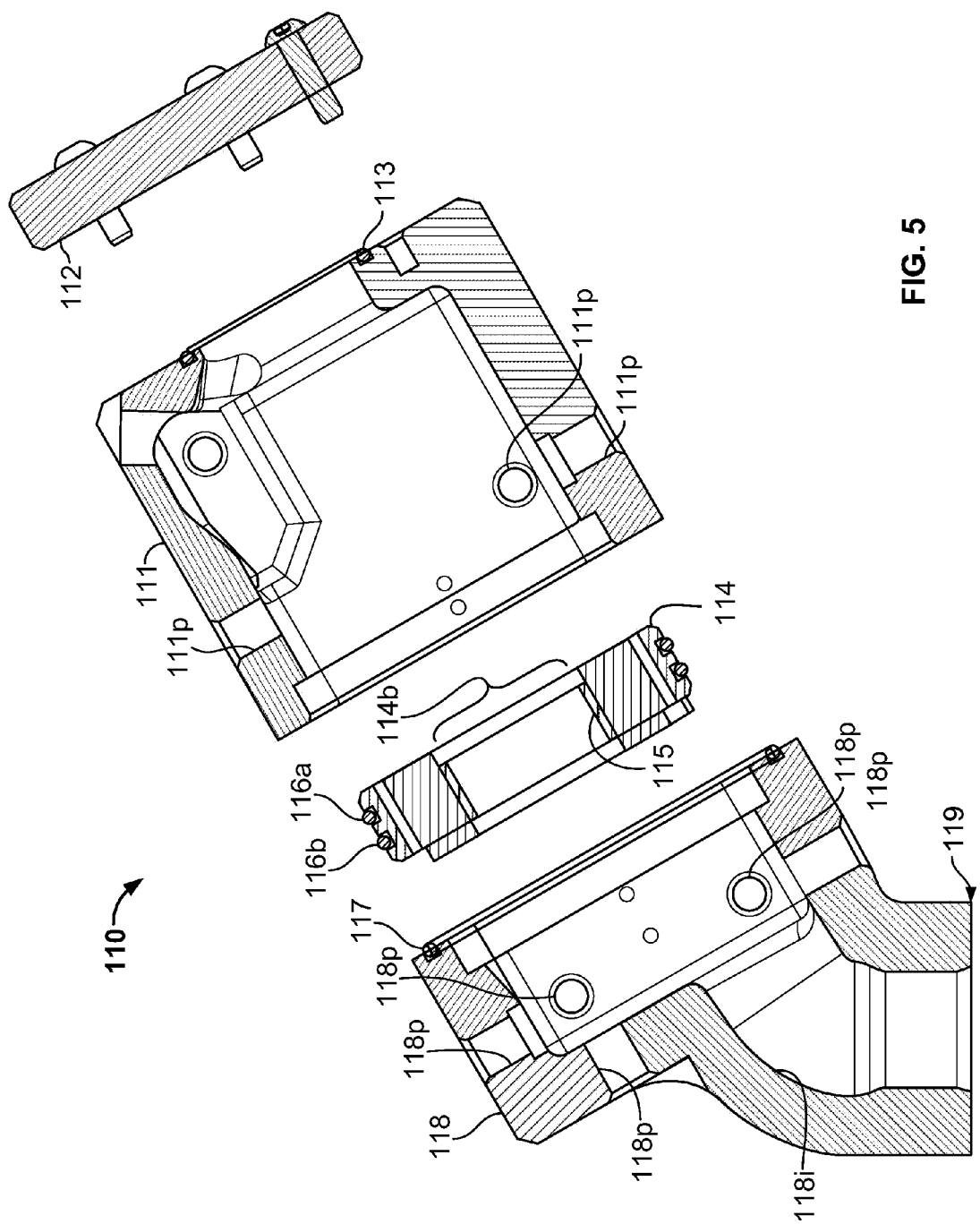
FIG. 5 is an exploded view of the test chamber of FIG. 4B.

Referring to FIGS. 4A, 4B, and 5, the chamber 110 includes a distal chamber 111, a valve holder 114, and a proximal chamber 118. When the chamber 110 is assembled, the valve holder 114 is disposed between the distal chamber 111 and the proximal chamber 118. An end portion 119 of the proximal chamber 118 can be coupled to a bellows (e.g., the bellows 130 of the ALT system 100). In such a case, an extension or compression of the bellows can withdraw or propel a volume of liquid in relation to the chamber 110 such that the volume of liquid is transferred between the proximal and distal chambers 111 and 118. In that case, the volume of liquid passes through the valve holder 114. To facilitate the passage of liquid, the distal chamber 111 includes a compliancy feature (e.g., airspace 182 as described below in reference to FIG. 7, or another type of compliancy feature such as, but not limited to, a flexible member).

In some embodiments, the components of the chamber 110 are made of polymeric materials. For example, in some embodiments the components of the chamber 110 are made of polymeric materials such as, but not limited to, polycarbonate (e.g., LEXAN), polyoxymethylene (e.g., DELRIN), acrylic, acetyl, PVC, and the like. Such materials can be formed into the required shapes by machining, molding, 3D printing, and/or by any other suitable processes and combinations of processes. In some embodiments, transparent or near transparent materials are used for components of the chamber 110 (e.g., at least the proximal and distal chambers 111 and 118). As such, the interior of the chamber 110 can be advantageously visible in some embodiments. In some embodiments, three or more sides of the chamber 110 assembly are substantially transparent.

The distal chamber 111 is releasably coupled to the proximal chamber 118. In some embodiments, one or more latches, clamps, pins, hinges, threaded connections, bayonet connections, circumferential clamps, and/or other types of quick release joining mechanisms are used to releasably couple the distal chamber 111 to the proximal chamber 118 in a convenient manner. Such user-friendly mechanisms for assembling and disassembling the chamber 110 can be desirable because at certain times during valve durability testing the chamber 110 may need to be disassembled so that other types of tests or inspections can be performed on the valves.

In the depicted embodiment, a lens 112 is attached to the distal chamber 111. The lens 112 can be a transparent member such as polycarbonate, tempered glass, and the like. The lens 112 can provide a direct view of a valve located within the valve holder 114. While in the depicted embodiment, the lens 112 is a separate component that is attached to the distal chamber 111, in other embodiments the lens 112 can be integrally formed in the wall of the distal chamber 111.

To make the chamber 110 a liquid tight enclosure, seals can be included at the interface between various components of the chamber 110. For example, a seal 117 is located at the interface between the distal chamber 111 and the proximal chamber 118. Also, a seal 113 is located at the interface between the distal chamber 111 and the lens 112. One or more seals 116a and 116b can also be located around the periphery of the valve holder 114. The seals 116a and 116b can inhibit paravalvular leaks between the distal chamber 111 and the proximal chamber 118. In some embodiments, one or more seals can also be located at the interface between the end portion 119 of the proximal chamber 118 and the bellows. The seals can be constructed as O-rings, D-rings, washers, gaskets, and the like, and can be made of materials such as, but not limited to, ethylene propylene diene monomer (EPDM), Nitrile, silicone, fluorocarbons, polyurethane, neoprene, fluorinated ethylene propylene (FEP), and the like.

One or more ports 111p can be included in the distal chamber 111. Similarly, one or more ports 118p can be included in the proximal chamber 118. Such ports 111p and 118p can be used to access the interior open spaces that are defined by the chambers 111 and 118 respectively. The ports 111p and 118p can be used for various purposes such as, but not limited to, draining liquid from within the chambers 111 and 118, mounting one or more sensors within the chambers 111 and 118, attaching a compliance chamber to the proximal chamber 118 and/or the distal chamber 111, and mounting one or more lights for illuminating the interior of the chambers 111 and 118. For example, in some cases the ports 111p and 118p can be used to mount pressure sensors that are used for monitoring the pressure of the liquid within the chambers 111 and 118. In addition, in some cases the ports 111p and 118p can be used to mount lights (e.g., LEDs) that can be used to enhance the viewing of a valve that is undergoing testing. For example, as will be described further below, in some embodiments such lights can be used as timing lights so that the high-speed operation of the valve undergoing testing can be observed as if it were operating at a slower speed.

The proximal chamber 118 includes an inlet passageway 118i. The inlet passageway 118i conveys liquid between the bellows and the chambers 111 and 118. In some embodiments, the inlet passageway 118i is configured to convey a jet of liquid from the bellows to the proximal chamber 118 that flows substantially coaxial to the central axis of the valve holder 114. In the depicted embodiment, to achieve the substantially coaxial flow the inlet passageway 118*i* is radiused and positioned such that the outer radius of the inlet passageway 118*i* is approximately aligned with the axis of the central axis of the valve holder 114. In some embodiments, other configurations of the inlet passageway 118*i* in relation to the valve holder 114 can be used.

The valve holder 114 includes a central bore 114*b* that is lined with a removable sleeve 115. The inner diameter of the sleeve 115 is configured to receive a valve body therein. The interface between the inner diameter of the sleeve 115 and the outer diameter of the valve body is intended to be substantially liquid-tight to avoid paravalvular leaks during testing. Thus, the sleeve 115 can be made of a compliant material. For example, in some embodiments the sleeve 115 can be made of materials such as, but not limited to, silicone, neoprene, and other suitable elastomers. In some embodiments, the inner diameter of the sleeve 115 may include a circumferential groove or other such surface features to facilitate mounting the valve to be tested therein. In particular embodiments, the inner diameter of the sleeve 115 may be designed to simulate the geometry (physiology) of a valve implant site. In some embodiments, the sleeve 115 is compliant such that if the valve ΔP reaches an over-peak condition, the compliance may reduce the effects of the condition. That is, in some embodiments the sleeve 115 is configured to deflect in response to a high ΔP between the proximal interior space and the distal interior space of the chamber 110.

Referring to FIGS. 6A and 6B, the valve holder 114 can receive an example prosthetic heart valve 150 within the central bore 114*b* of the valve holder 114. The valve 150 is a one-way valve. That is, liquid flowing in one direction in relation to the valve 150 will open the valve 150 so that the liquid can flow therethrough (e.g., referring to FIGS. 4A and 4B, as liquid flows from the proximal chamber 118 towards the distal chamber 111 the valve 150 will open). However, when the liquid starts to flow in the opposite direction in relation to the valve 150, the valve 150 will close such that the liquid will be prevented from flowing therethrough. Alternatively, in some embodiments the valve 150 is mounted in the opposite direction such that the valve 150 will close when liquid is transferred from the proximal chamber 118 to the distal chamber 111, and the valve 150 will be forced open when liquid is transferred from the distal chamber 111 to the proximal chamber 118.

To facilitate liquid flow through the valve holder 114 in the direction which causes the valve 150 to be closed, the valve holder 114 includes one or more return flow orifices 114*ou* and 114*ol*. In the depicted embodiment, the return flow orifice 114*ou* is an upper orifice, and the return flow orifice 114*ol* is a lower orifice. Having an upper orifice 114*ou* and a lower orifice 114*ol* can be advantageous in some embodiments. For example, the upper orifice 114*ou* can facilitate airflow therethrough in the event that some air (e.g., bubbles) becomes entrapped in the proximal chamber 118 (as will be explained further below, some entrapped air can be better accommodated in the distal chamber 111). Further, the lower orifice 114*ol* can facilitate fluid flow therethrough to assist with gravitational drainage of the liquid from the chambers 118 and 111. Accordingly, in some embodiments one or more return flow orifices are positioned on the valve holder 114 such that at least a first return flow orifice of the one or more return flow orifices 114*ou* and 114*ol* is located in an upper portion of the chamber 111 and 118, and at least a second return flow orifice of the one or more return flow orifices 114*ou* and 114*ol* is located in a lower portion of the chamber 111 and 118.

While the depicted embodiment includes two return flow orifices 114*ou* and 114*ol*, in some embodiments a single orifice or more than two orifices are included. For example, in some embodiments the valve holder 114 can include three, four, five, six, seven, eight, nine, ten, or more than ten orifices.

In the depicted embodiment, an interchangeable valve holder end plate 114*p* is included. In some embodiments, one purpose of the valve holder end plate 114*p* can be to configure the valve holder 114 to have a desired number of return flow orifices. In addition, in some embodiments another purpose of the valve holder end plate 114*p* can be to configure the sizes of the one or more return flow orifices. While in the depicted embodiment the return flow orifices 114*ou* and 114*ol* are located in the valve holder 114, it should be understood that, additionally or alternatively, in some embodiments return flow orifices can be located in other structures of the chamber 110. For example, in some embodiments the return flow pathway can be connected between the ports 118*p* and 111*p*.

It should be understood that, as will be described further below, the quantity and size of the one or more return flow orifices (e.g., orifices 114*ou* and 114*ol*) influences the pressure differential between the proximal and distal chambers 118 and 111 (refer to FIGS. 4A and 4B). This pressure differential is also the pressure that the valve 150 is exposed to when the valve 150 is closed.

Briefly, the effect that the quantity and size of the one or more return flow orifices have on the differential pressure is explained as follows. An amount of liquid will be transferred through the open valve 150 as the bellows 130 compresses (e.g., refer to FIGS. 1-3). In general, the ALT system will be configured such that the amount of liquid to be transferred will be that amount that is needed to sufficiently open the valve. That same amount will need to be returned through the return flow orifices, and within a particular period of time (the time during which the bellows 130 is extending). Therefore, a small total area of return orifice will result in a higher differential pressure, while a large total area of return orifice size will result in a lower differential pressure. In this fashion, selection of the quantity and/or size of the return flow orifices can influence the pressure that the valve 150 is exposed to when the valve 150 is closed. In some implementations, an open area of the one or more return flow orifices is selected based on a size of a valve 150 to be tested.

In some embodiments, the total area of return flow orifices is adjustable without disassembling the chamber 110 (refer to FIGS. 4A and 4B). For example, in some embodiments one or more of the return flow orifices can be configured as a valve-like device (e.g., a gate valve, ball valve, needle valve, etc.) that can be adjusted externally to the chamber 110. In some embodiments, the adjustment can be performed manually, including while the test system is operating. In particular embodiments, the adjustment can be performed automatically. In some such embodiments, a valve actuator and controls can be included such that automated adjustments of the total area of return flow orifices can be made to control towards a target operating parameter such as, but not limited to, the differential pressure characteristic across the valve 150 when the valve 150 is closed (e.g., the peak differential pressure across the valve 150 when the valve 150 is closed).

Figure 7:
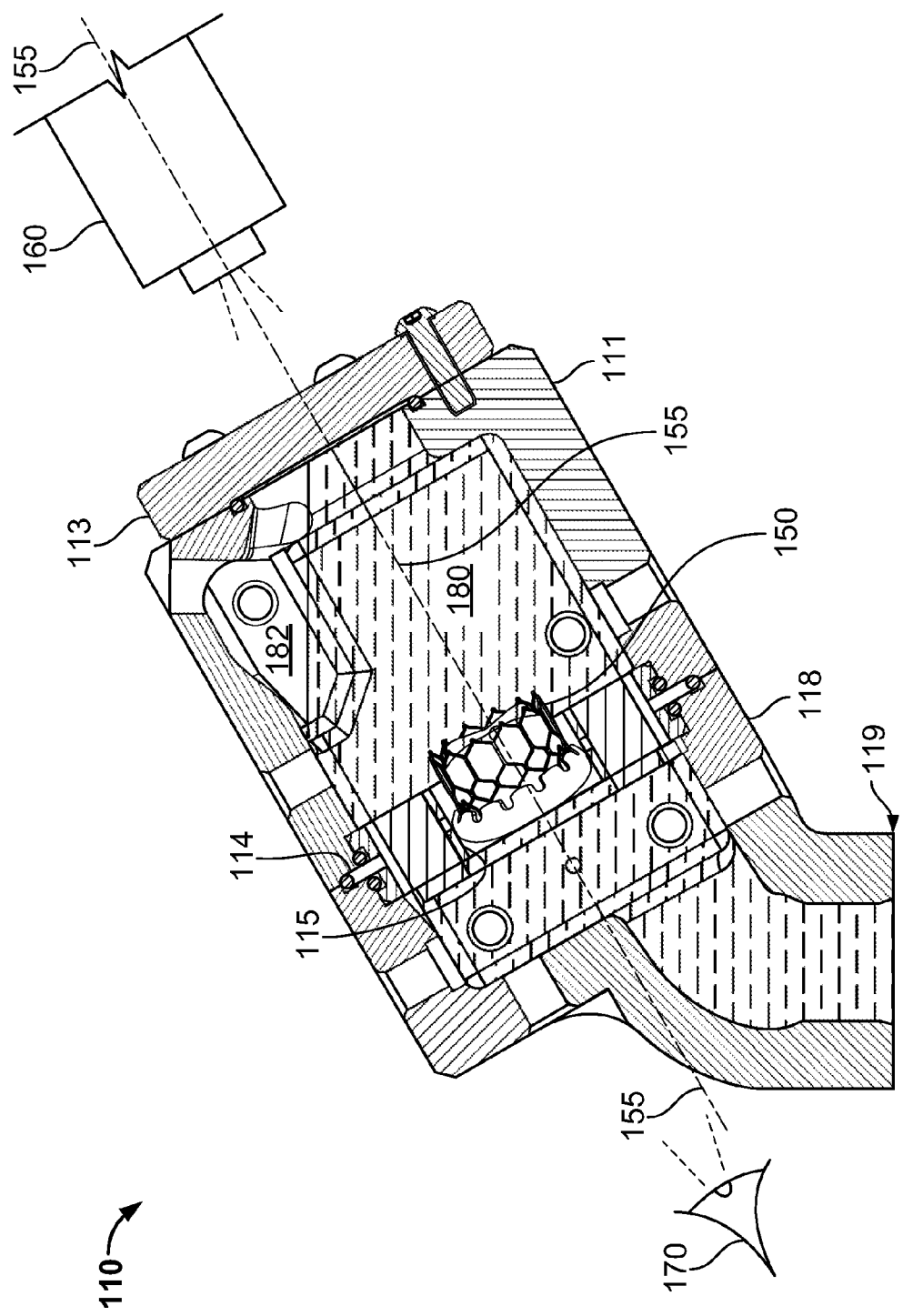
FIG. 7 is a side view of the test chamber of FIG. 4B that is depicted partially filled with a liquid and undergoing visual inspection.

Referring to FIG. 7, in some embodiments the chamber 110 can be filled with a liquid 180 and an airspace 182. The airspace 182 is located in the distal chamber 111 and is in direct contact with the liquid 180. The liquid 180 can be liquids such as, but not limited to, water, saline, culture media, and the like. The airspace 182 can be filled with a gas such as air, $CO_2$, and the like. While the volume of liquid 180 is essentially incompressible, the volume of the airspace 182 is compressible.

During operation of the chamber 110, the airspace 182 is cyclically compressed and decompressed in synch with the cyclical motion of the bellows 130 (refer to FIGS. 4A and 4B). That cyclic compression and decompression of the airspace 182 occurs as follows. As the bellows 130 compresses, some of the liquid 180 from the bellows 130 is expelled into the proximal chamber 118. The liquid 180 that is expelled into the proximal chamber 118, in turn, causes a same amount of liquid 180 to flow through the valve 150 and return flow orifices into the distal chamber 111. That flow of liquid 180 causes the valve 150 to open. Due to the amount of liquid 180 that flowed into the distal chamber 111, the volume of the airspace 182 decreases equivalently. The aforementioned actions continue until the bellows 130 ends its compression phase.

After the compression phase of the bellows 130, the bellows 130 begins to extend. As the bellows 130 extends, some amount of liquid 180 is drawn out of the chamber 110. In total, the same amount of liquid 180 that was expelled from the bellows 130 during its compression phase will be drawn out of the chamber 110 and return back into the bellows 130 during the bellow's 130 extension phase. That removal of the liquid 180 from the chamber 110 will result in an equivalent increase in the volume of the airspace 182.

From the foregoing description regarding the liquid 180 and the airspace 182, it should be understood that in some embodiments the airspace 182 functions like a gas spring. That is, the airspace 182 is compressed during a portion of the test cycle and expanded during another portion of the test cycle.

It can also be understood that the nominal volume of the airspace 182 will affect the force required from the bellows 130 to drive the liquid 180 during the compression phase of the bellows 130. For example, less work will be required by the bellows 130 to compress the airspace 182 if the airspace 182 is larger than if the airspace 182 is smaller. That is true because, in accordance with the ideal gas law, compressing a large airspace 182 by a volumetric amount will result in a smaller pressure increase of the airspace 182 than will compressing a small airspace 182 by the same volumetric amount. The compressed airspace 182 can also facilitate flow of the liquid 180 from the distal chamber 111 to the proximal chamber 118 via the return flow orifices 114*ou* and 114*ol* (refer to FIG. 6B) during the extension of the bellows 130. A negative pressure gradient across the valve 150 during and after closing of the valve 150 is desired for the functional test of the valve 150. The positive pressure within the airspace 182 and the negative pressure created by the extension of the bellows 130 facilitate that negative pressure across the valve 150. In some circumstances, this can serve to reduce the amount of vacuum pulled by the bellows 130 during testing.

Using the aforementioned principles regarding the airspace 182, the volume of the airspace 182 can be selected (as one factor) to provide a desired pressure operation range of the test system 100. For example, the maximum pressure that the liquid 180 will attain (at the end of the compression of the bellows 130) is affected by the nominal size of the airspace 182. The change in volume of the airspace 182 throughout the compressional stroke of the bellows 130, relative to the nominal size of the airspace 182 at least partly defines the maximum pressure (e.g., a 1 ml volume change of a 2 ml airspace 182 will produce greater pressures than a 2 ml volume change of a 20 ml airspace 182). In some implementations, the airspace 182 is sized such that the maximum pressure of the liquid 180 is relatively similar to the maximum pressure that the valve being tested will be exposed to in expected usage scenarios. For example, the maximum pressure that an aortic heart valve will be exposed to is the systolic pressure (e.g., nominally about 120 mmHg to about 160 mmHg). Therefore, in one example the volumetric size of the airspace 182 may be selected so that the maximum pressure of the liquid 180 is about 150 mmHg during the systolic phase. In other examples, other pressure levels can be designed for by selecting a suitable volumetric size of the airspace 182.

In some embodiments, one or more heating elements (not shown) and one or more temperature sensors (not shown) are included to provide the ability to control and measurement of the liquid 180. Such heating elements and temperature sensors can be located in various locations such as, but not limited to, near the interface between the end portion 119 of the proximal chamber 118 and the bellows. The heating elements and temperature sensors may also be positioned in other locations such that the temperature of the liquid 180 can be measured and/or controlled as desired.

Still referring to FIG. 7, in the depicted embodiment a longitudinal axis 155 of the chamber 110 is tilted at an angle of about 35° from horizontal. In other embodiments, angles of about 0° to about 20°, or about 15° to about 35°, or about 30° to about 50°, or about 45° to about 65°, or about 60° to about 80°, or about 75° to about 90° can be used.

In some embodiments, the tilt of the longitudinal axis 155 provides some benefits. For example, if any air becomes inadvertently entrained within the liquid 180, the air will tend to ascend towards the airspace 182 since the airspace 182 is at the highest elevation within the chamber 110. The inadvertently entrained air will tend to have a less negative impact on the testing if the inadvertently entrained air resides within the airspace 182 rather than in other places within the chamber 110. In another example, the tilt of the longitudinal axis 155 can allow for observation of both the top and the bottom of the valve 150. That is, as represented by an eye symbol 170, an observation of the bottom of the valve 150 can be made through the end wall of the proximal chamber 118. Further, the ergonomics associated with viewing of the valve 150 is benefitted by the tilt of the longitudinal axis 155. In addition, as represented by a camera 160, an observation of the top of the valve 150 can be made through the end wall of the distal chamber 118.

The camera 160 can be used to view the operation of the valve 150 during the testing. The camera 160 can be a still frame camera or a video camera. In some embodiments the camera 160 is a high-speed video camera. As described previously, in some embodiments one or more lights for illuminating the interior of the chambers 111 and 118, and the valve 150 are included. For example, in some embodiments such lights can be used as timing lights so that the high-speed operation of the valve 150 can be observed by the camera 160 as if it were operating at a slower speed.

In some embodiments, the camera 160 can be part of a machine vision system. In some such embodiments, the camera 160 and machine vision system can be used to determine the extent to which the valve 150 opens during testing (e.g., a number of pixels corresponding to an open area of the valve 150 can be quantified). The openness (also referred to herein as the effective open area) of the valve 150 may be a parameter that needs to be verified during the performance of some durability testing protocols. Further, by connecting the camera 160 and machine vision system to a control system of the test system 100, closed-loop control using the machine vision system can be performed in some embodiments. For example, the test system 100 control system can automatically adjust the operation of the test system 100 to attain a threshold level of open area of valve 150 in some embodiments. Furthermore, it should be understood that such a machine vision system can be used to detect valve failure through user interaction or automatically through a closed-loop control.

Figure 8:
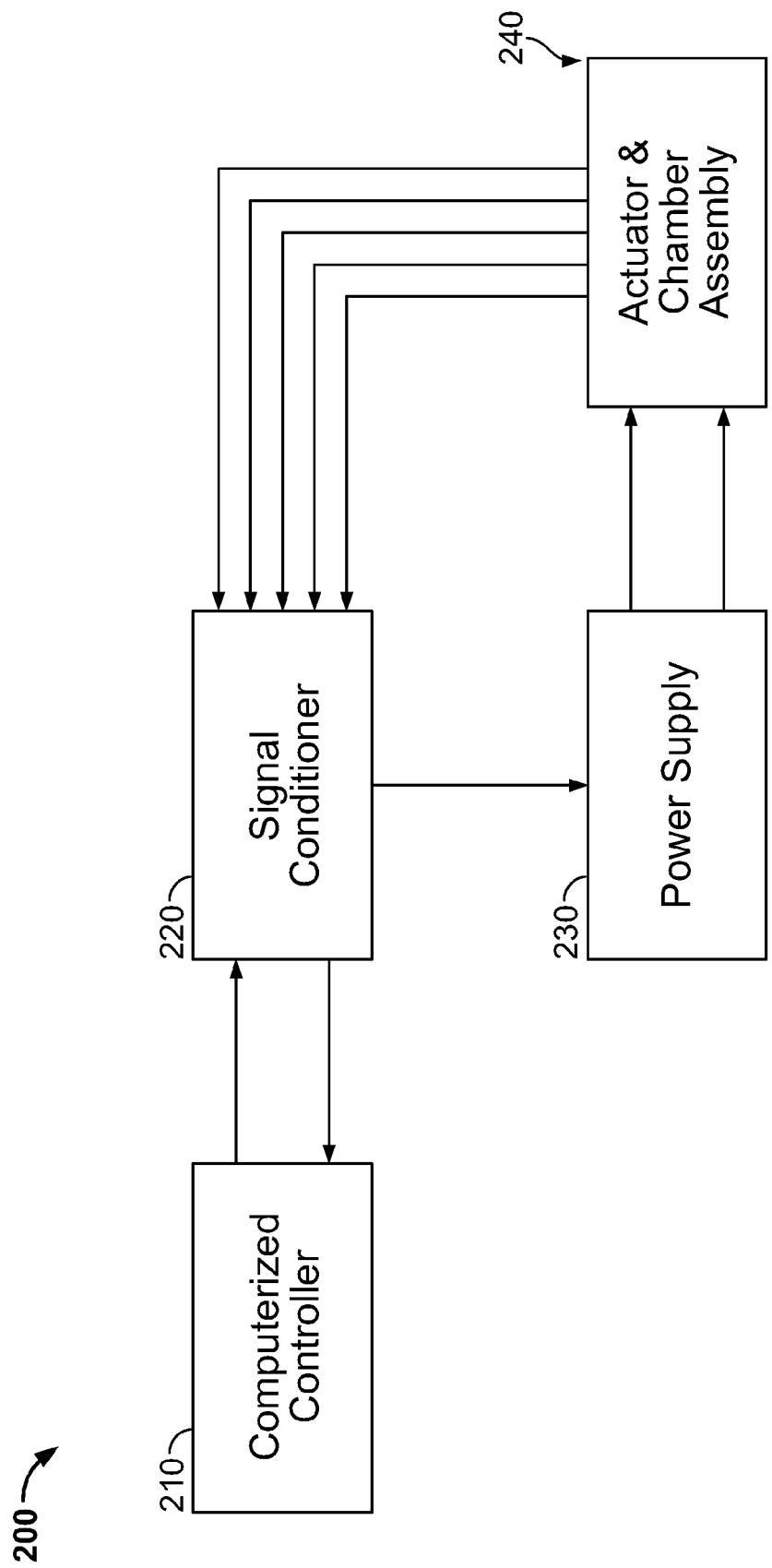
FIG. 8 is a block diagram of the accelerated life testing system of FIG. 1.

Referring to FIG. 8, a control system 200 for the ALT systems provided herein can include a computerized controller 210, a signal conditioner 220, a power supply 230 (which can include an amplifier stage in some embodiments), and an actuator and chamber assembly 240. The components of the control system 200 are in electrical communication with each other. That is, the component of the control system 200 can provide various outputs and receive various inputs from each other so that the overall control system 200 functions as desired. The components shown here, their connections and relationships, and their functions, are meant to be exemplary only, and are not meant to limit implementations of the inventions described and/or claimed in this document.

The control system 200 includes the computerized controller 210. The computerized controller 210 can be various forms of a digital computer, such as a laptop, desktop, workstation, PLC, server, mainframe, micro-controller, and other appropriate computers and combinations of computers or computer parts. The computerized controller 210 can include one or more processors, various formats of memory (volatile, non-volatile, hard disc, etc.), a GUI, various interface and communication devices and ports, and so on. Such devices may be interconnected using various busses, and may be mounted on a common motherboard or in other manners as appropriate. The one or more processors can process instructions for execution within the computerized controller 210, including executable instructions stored in the memory.

The one or more processors of the computerized controller 210 may communicate with a user through a control interface and a display interface coupled to the display device. The display device may be, for example, a TFT (Thin-Film-Transistor Liquid Crystal Display) display or an OLED (Organic Light Emitting Diode) display, or other appropriate display technology. The display interface may comprise appropriate circuitry for driving the display to present graphical and other information to a user. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input. The control interface may receive commands from a user and convert them for submission to the one or more processors. In addition, an external interface may provide communication with the one or more processors, to enable near area communication of the computerized controller 210 with other devices. The external interface may provide, for example, for wired communication in some implementations, or for wireless communication in other implementations, and multiple interfaces may also be used.

The control system 200 also includes the signal conditioner 220. The signal conditioner 220 can be configured to receive signals from various sensors, (e.g., pressure or temperature sensors) and to manipulate the signals for reception by the computerized controller 210. For example, in some embodiments the signal conditioner 220 may convert analog signal inputs to digital signals to be received by the computerized controller 210. In addition, the signal conditioner 220 may perform other signal conversion activities such as amplification, filtering, isolation, and the like. Further, in some embodiments the signal conditioner 220 may receive inputs from the computerized controller 210, which are then converted for receipt for another device such as the power supply 230 (which can include a power amplifier in some embodiments).

The control system 200 also includes the power supply 230. The power supply 230 provides electrical power to the actuator and chamber assembly 240 to drive the actuator (e.g., the electromagnetic actuator 140 of FIG. 3). For example, the power supply 230 can receive an input signal from the signal conditioner 220, and the power supply 230 can, in turn, amplify the signal and send it to the actuator and chamber assembly 240. In some embodiments, the signal can be a waveform (e.g., a sine wave or another shape). The power supply 230 can also provide electrical power for a liquid heater located in the actuator and chamber assembly 240 in some embodiments.

The control system 200 also includes the actuator and chamber assembly 240. In some embodiments, the actuator and chamber assembly 240 can be exemplified as the system 100 as described above (refer to FIGS. 1-3), for example. The actuator and chamber assembly 240 can receive the aforementioned inputs from the power supply 230, and can provide one or more outputs to the signal conditioner 220. For example, such outputs can include, but are not limited to, one or more of the following (referring to FIGS. 1-7): a pressure of the proximal chamber 118, a pressure of the distal chamber 111, a temperature of the liquid 180, a displacement of the electromagnetic actuator 140, an output from the camera 160 and machine vision system that indicates an openness of the valve 150, and the like. Such output signals can be received by the signal conditioner 220, converted as necessary, and passed on to the computerized controller 210. The computerized controller 210 can use the output signals as parameters in the control algorithms being run by the controller 210. The control algorithms can, in turn, generate updated control signals that can be output to the signal conditioner 220 as described above. In this manner, the control system 200 can operate an ALT system in a controlled fashion as desired. In some embodiments, each testing chamber has its own micro-controller for monitoring and controlling testing parameters (as slave systems) that are connected to a master system (e.g., a laptop computer, etc.), that at least periodically monitors the micro-controllers.

Figure 9A:
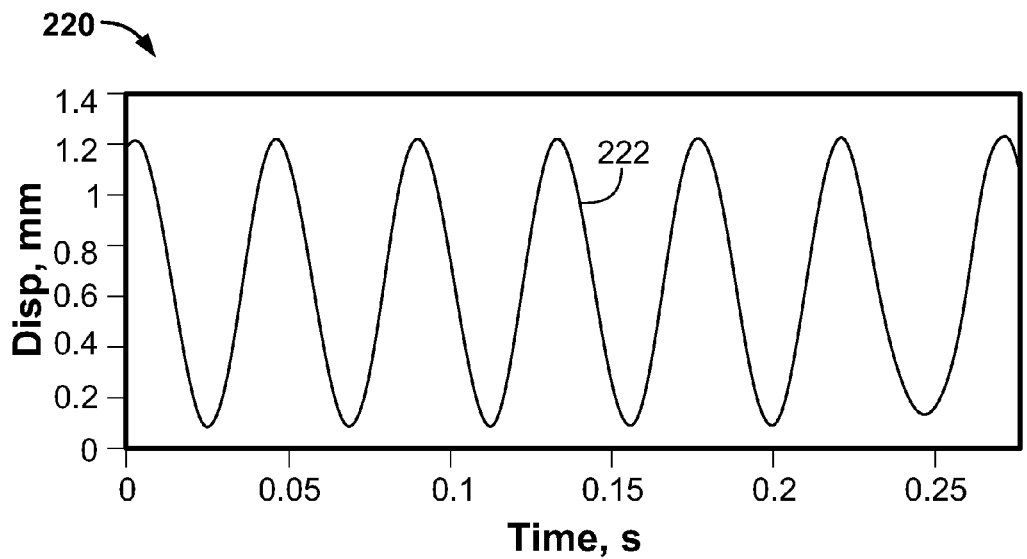
FIG. 9A is an example input waveform that can be used for the accelerated life testing systems in accordance with some embodiments.

Referring to FIG. 9A, a graph 220 of actuator displacement versus time can illustrate an example input waveform 222 that can be used for system 100. The example waveform 222 is essentially a sine wave. However, in some embodiments other shapes of input waveforms 222 can be used. Further, the cyclic rate shown is just an example, faster and slower cyclic rates are envisioned within the scope of this disclosure. Additionally, it should be understood that the magnitude of the wave signal, peak and valley values, and mean value are flexible and can be adjusted to achieve the desired pressure and volume flow profile for testing.

Figure 9B:
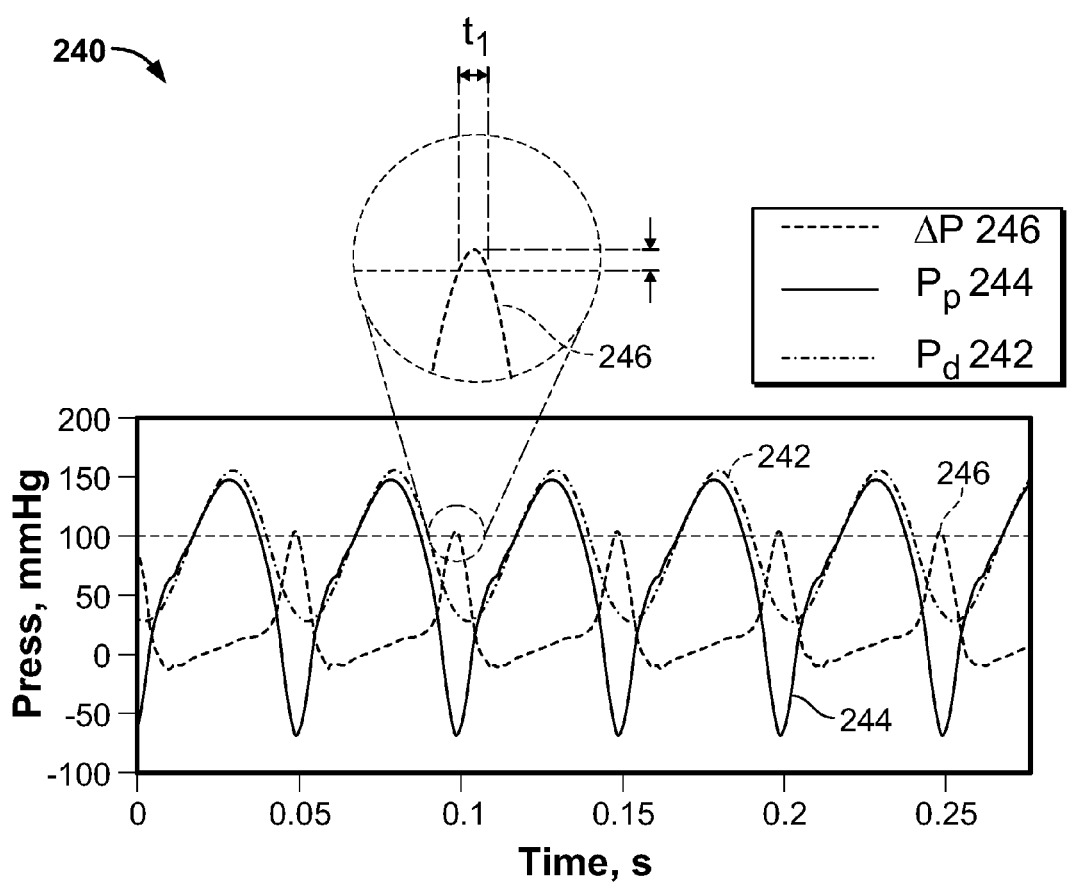
FIG. 9B are example waveforms of test chamber pressures and the test chamber differential pressure in accordance with some embodiments.

The input waveform 222 is indicative of the movement of the electromagnetic actuator 140, the bellows 130, and the flow of the liquid 180 (referring to FIGS. 1-7). Referring now to FIGS. 9A and 9B, it can be seen that the input waveform 222 causes corresponding fluctuations in a distal pressure curve 242, a proximal pressure curve 244, and a differential pressure curve 246. The distal pressure curve 242 represents the pressure of the liquid 180 in the distal chamber 111. The proximal pressure curve 244 represents the pressure of the liquid 180 in the proximal chamber 118. The differential pressure curve 246 represents the differences between the pressures 242 and 244 of the distal chamber 111 and the proximal chamber 118.

The fluctuations of the pressure curves 242 and 244 can be described, briefly, as follows (also referring to FIGS. 1-7). The pressure curves 242 and 244 rise as the bellows 130 axially contracts. The axial compression of the bellows 130 forces some amount of the liquid 180 to expel from the bellows 130 into the chamber 110. The flow of the liquid 180 in the direction from the proximal chamber 118 to the distal chamber 111 causes the valve 150 to open. Because the valve 150 is a relatively large opening, the pressure curves 242 and 244 rise substantially following the same curve, and the differential pressure curve 246 is near zero. As the bellows 130 reverses and begins to axially extend, some amount of liquid 180 begins to be drawn back into the bellows 130 from the chamber 110. After the valve 150 closes, the liquid 180 must flow through the one or more return flow orifices 114*ou* and 114*ol*. The one or more return flow orifices 114*ou* and 114*ol*, being relatively small, cause a significant pressure drop in the proximal chamber 118 as the liquid 180 flows through the one or more return flow orifices 114*ou* and 114*ol*. Therefore, the proximal pressure curve 244 (proximal chamber 118) drops below the distal pressure curve 242 (distal chamber 111), and the differential pressure curve 246 rises correspondingly. The differential pressure curve 246 is the pressure across the valve 150 as a function of time.

From the foregoing description, it can be understood that the pressure across the valve 150 is affected by the pressure drop of the liquid 180 as it flows through the one or more return flow orifices 114*ou* and 114*ol*. Additionally, as described above, the pressure drop of the liquid 180 as it flows through the one or more return flow orifices 114*ou* and 114*ol* is affected by the size and quantity of the one or more return flow orifices 114*ou* and 114*ol*. Therefore, it holds that the pressure across the valve 150 is affected by the size and quantity of the one or more return flow orifices 114*ou* and 114*ol*. In some implementations of system 100, it is desirable to substantially replicate the physiological conditions in which the valve 150 will be used. Therefore, for the prosthetic heart valve 150, the size and quantity of the one or more return flow orifices 114*ou* and 114*ol* can be selected to create a differential pressure curve 246 substantially as shown (the pressure across the valve 150 is essentially 0 mm Hg when the valve 150 is open, and at least 100 mmHg for part of the time when the valve 150 is closed).

As stated in the Background, 5840-3:2013 requires that, during at least 5% of each cycle, the differential pressure across the valve must be at least a specified pressure (e.g., 100 mmHg for an aortic valve). The enlarged portion of FIG. 9B shows an example of how the differential pressure curve 246 relates to that requirement. In other words, during a time period $t_1$, the differential pressure curve 246 is at or above 100 mmHg (using the specified pressure for an aortic valve as an example), where time period $t_1$ is at least 5% of each cycle time T. In some cases during $t_1$, the differential pressure curve 246 may exceed 100 mmHg, up to a maximum differential pressure $p_1$. In general, it can be desirable to have a differential pressure curve 246 with a $p_1$ that is not substantially greater than 100 mmHg. That is the case because when $p_1$ is substantially greater than 100 mmHg, the valve 150 is being stressed more than what is required by ISO 5840:2005 (or as required by other applicable standards or relevant test conditions).

In some embodiments, the system 100 can be tuned to produce a differential pressure curve 246 that (i) meets the requirement that, during at least 5% of each cycle, the differential pressure across the valve must be at least a specified pressure (e.g., 100 mmHg for an aortic valve) and that (ii) has a $p_1$ that is not substantially greater than the specified pressure. Such tuning can be performed by selecting an appropriate combination of factors such as, but not limited to: the size and quantity of the one or more return flow orifices 114*ou* and 114*ol*, the cycle speed, the shape of the input waveform 222, the shape of the chamber 110, the volume of liquid 180 that is displaced during the cycle, the size and pressure of the airspace 182, and by locating the one or more return flow orifices 114*ou* and 114*ol* between the distal chamber 118 and the proximal chamber 111 such that there is a short return flow path therebetween.

Figure 10:
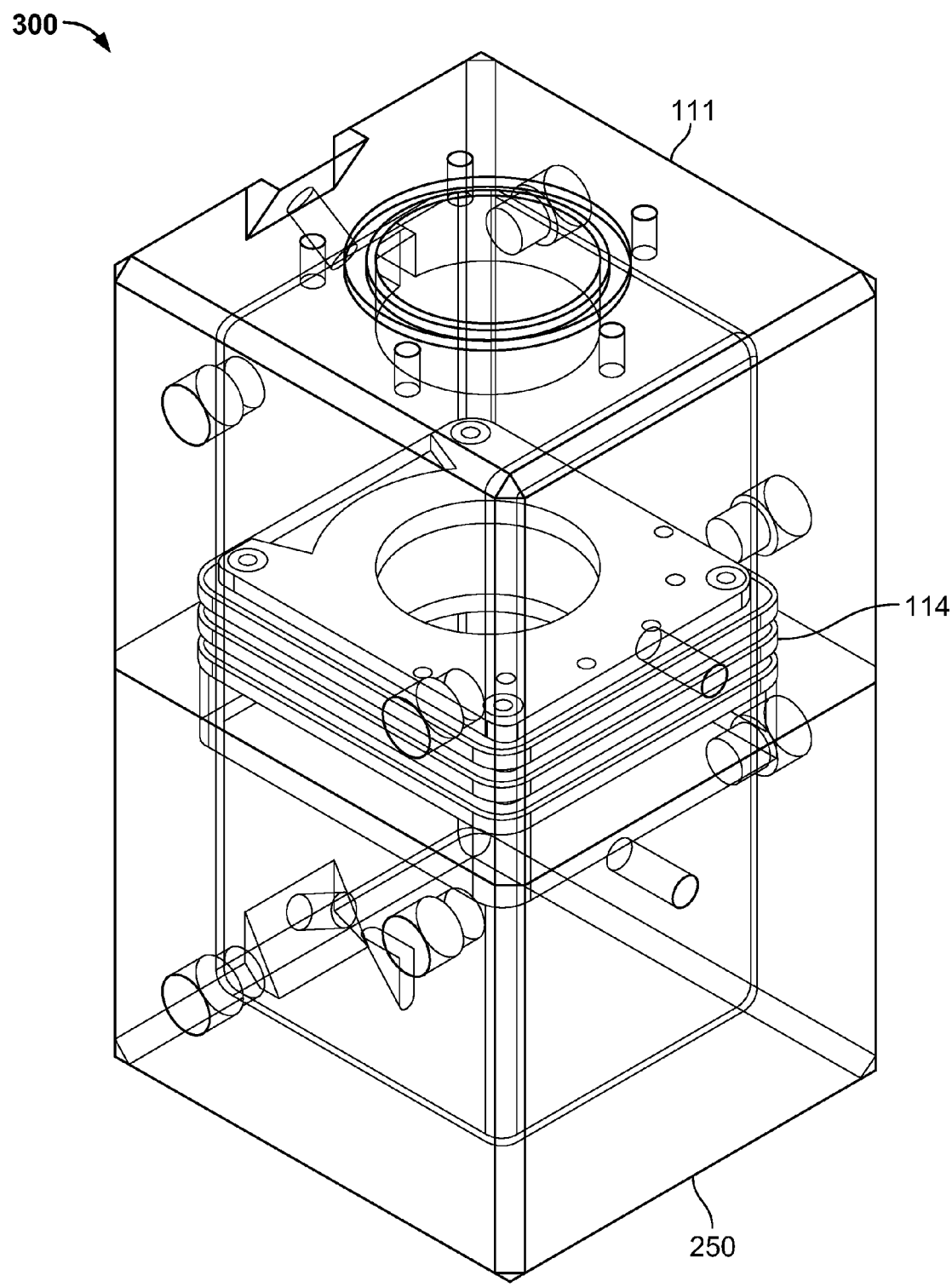
FIG. 10 is an isometric view of an example portable portion of a test chamber including the valve holder.

Referring to FIG. 10, a portable test chamber assembly 300 can include the distal chamber 111, the valve holder 114, and a chamber cap 250. The portable test chamber assembly 300 can provide a convenient way to transport a valve and test chamber arrangement between various test stands (e.g., between durability testing and pulse duplication testing apparatuses, for example). Further, the portable test chamber assembly 300 can allow a user to assemble a valve with the valve holder 114 and with a distal chamber 111, and then to store the assembly by attaching the chamber cap 250. In some cases, a liquid can be added such that the valve can be immersed in the liquid during transport or storage. By using the portable test chamber assembly 300, more efficient set up and management of the overall testing process can be obtained. In some embodiments, the chamber assembly 300 can be used for static incubation of a valve that is cell-seeded until the cells/structure is at a state where the tissue can withstand some mechanical loading. In some embodiments, the chamber assembly 300 can be used to allow simulation of surgical implantation of transcatheter valves or similar, for example.

Referring to FIG. 11, an example cylindrical test chamber 400 embodiment can include a base 402, a proximal chamber 410, a distal chamber 420, a valve holder 430, and an airspace 440. The cylindrical test chamber 400 is configured to be useable with the other relevant components of the system 100, such as the framework 120, the bellows 130, and the actuator 140 (refer to FIG. 3). The cylindrical test chamber 400 has a cylindrical chamber shape (whereas the chamber 110 has a three dimensional rectangular shape). While in the depicted embodiment the cylindrical test chamber 400 is vertically arranged, in some embodiments the cylindrical test chamber 400 can be tilted as described above in regard to the chamber 110. The cylindrical test chamber 400 can also include one or more of the other features described above in regard to the chamber 110.

Referring to FIG. 12, an example hexagonal test chamber 500 embodiment can include a base 502, a proximal chamber 510, a distal chamber 520, and a valve holder 530 (an airspace can be included in the distal chamber 520 when the hexagonal test chamber 500 contains a liquid). The hexagonal test chamber 500 is configured to be useable with the other relevant components of the system 100, such as the framework 120, the bellows 130, and the actuator 140 (refer to FIG. 3). The hexagonal test chamber 500 has a three dimensional hexagonal chamber shape (whereas the chamber 110 has a three dimensional rectangular shape). In the depicted embodiment, the hexagonal test chamber 500 is tilted as described above in regard to the chamber 110. The hexagonal test chamber 500 can also include one or more of the other features described above in regard to the chamber 110.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. As an additional example, test parameters might be controlled by selecting any of the monitored parameters (e.g., actuator displacement 222, proximal pressure 244, distal pressure 242, pressure gradient 246, airspace 182, and others) as independent parameters and adjusting the remaining dependent parameters accordingly. In certain implementations, multitasking and parallel processing may be advantageous.

What is claimed is:

1. A chamber assembly for testing a valve, the chamber assembly comprising:
a proximal chamber portion that defines a proximal interior space;
a distal chamber portion that defines a distal interior space that is confluent with the proximal interior space; and
a valve holder that is disposed between the proximal interior space and the distal interior space, the valve holder configured to receive the valve in a bore of the valve holder, wherein the valve holder includes one or more return flow orifices such that the proximal interior space is in fluid communication with the distal interior space via the one or more return flow orifices.

2. The chamber assembly of claim 1, wherein the chamber assembly is configured such that when the chamber assembly is coupled to an accelerated life testing system, and when the valve is contained in the bore of the valve holder, a bottom of the valve and a top of the valve are both visible by an observer.

3. The chamber assembly of claim 1, wherein the chamber assembly defines a longitudinal axis, and the chamber assembly is configured such that when the chamber assembly is coupled to an accelerated life testing system the longitudinal axis is tilted at an angle in comparison to horizontal.

4. The chamber assembly of claim 3, wherein the angle has a value selected within a ranged defined between 20° and 70° from horizontal.

5. The chamber assembly of claim 1, wherein an open area of the one or more return flow orifices is adjustable without removing the valve holder from the chamber assembly.

6. The chamber assembly of claim 1, further comprising a first pressure sensor configured to measure a liquid pressure within the proximal interior space and a second pressure sensor configured to measure a liquid pressure within the distal interior space.

7. The chamber assembly of claim 1, further comprising one or more lights coupled to the chamber assembly and configured for illuminating the valve.

8. The chamber assembly of claim 1, wherein the distal chamber portion is releasably attachable to the proximal chamber portion.

9. The chamber assembly of claim 1, wherein the valve holder is removably disposed between the proximal interior space and the distal interior space.

10. The chamber assembly of claim 1, wherein the chamber assembly is configured for accelerated life testing of the valve.

11. The chamber assembly of claim 1, wherein the chamber assembly is configured to contain a liquid.

12. The chamber assembly of claim 1, wherein the one or more return flow orifices are positioned on the valve holder such that at least a first return flow orifice of the one or more return flow orifices is located in an upper portion of the chamber and at least a second return flow orifice of the one or more return flow orifices is located in a lower portion of the chamber.

13. The chamber assembly of claim 1, wherein the bore of the valve holder is at least partially defined by a compliant sleeve that is configured to receive the valve, and wherein the compliant sleeve is configured to deflect in response to a pressure differential between the proximal interior space and the distal interior space.

14. The chamber assembly of claim 13, further comprising an interchangeable valve holder end plate disposed on the valve holder.

15. The chamber assembly of claim 14, wherein the interchangeable valve holder end plate configures at least one of the number of the return flow orifices or the size of the return flow orifices of the valve holder.

16. The chamber assembly of claim 1, wherein three or more sides of the chamber assembly are substantially transparent.

17. The chamber assembly of claim 1, wherein an open area of the one or more return flow orifices is selected based on a size of a valve to be tested.

18. The chamber assembly of claim 1, further comprising a lens attached to or integrally formed in a wall of the distal chamber.

19. The chamber assembly of claim 1, wherein at least of the distal chamber or the proximal chamber comprises one or more ports formed therein, the one or more ports being configured and dimensioned to receive at least one of a pressure sensor or a light.

20. The chamber assembly of claim 1, wherein the distal chamber is releasably coupled to the proximal chamber via a quick release joining mechanism.

\* \* \* \* \*